US008622057B2

(12) United States Patent
Ujhazy et al.

(10) Patent No.: US 8,622,057 B2
(45) Date of Patent: Jan. 7, 2014

(54) METHODS AND APPARATUS FOR SUPPLYING CLEAN BREATHABLE GAS (75) Inventors: Anthony John Ujhazy, East Lindfield (AU); Jonathan Caldwell Wright, Clontarf (AU); Joanne Elizabeth Drew, Balgowlah Heights (AU); Michael Berthon-Jones, Leonay (AU)

(73) Assignee: ResMed Ltd (AU)

(*) Notice: Subject to any disclaimer, the term of this patent is extended or adjusted under 35 U.S.C. 154(b) by 2953 days.

(21) Appl. No.: 10/467,601

(22) PCT Filed: Feb. 15, 2002

(86) PCT No.: PCT/AU02/00161
§ 371 (c)(1),
(2), (4) Date: Jan. 22, 2004

(87) PCT Pub. No.: WO02/066105
PCT Pub. Date: Aug. 29, 2002

(65) Prior Publication Data
US 2004/0112381 A1    Jun. 17, 2004

(30) Foreign Application Priority Data
Feb. 16, 2001  (AU) .......................................... 3154

(51) Int. Cl.
A62B 7/10   (2006.01)
A62B 23/02  (2006.01)
A61M 16/00  (2006.01)

(52) U.S. Cl.
USPC ............ 128/204.23; 128/200.24; 128/203.13; 128/204.18; 128/204.21; 128/205.29; 128/205.27

(58) Field of Classification Search
USPC ............ 128/200.24, 203.13, 204.23, 204.26, 128/201.25, 203.12, 204.18, 204.29, 128/205.25, 206.21
See application file for complete search history.

(56) References Cited

U.S. PATENT DOCUMENTS 4,629,482 A   12/1986  Davis
4,685,944 A    8/1987  Allan et al.
(Continued)

FOREIGN PATENT DOCUMENTS

AU    719758     6/1998
DE    9317450 U1 6/1994
(Continued)

OTHER PUBLICATIONS

Beers, Mark H. and Robert Berkow Eds. "Section 6—Pulmonary Disorders-Asthma". The Merck Manual of Diagnosis and Therapy. 17th Edition. Merck Research Laboratories, 1999. p. 556.*

(Continued)

*Primary Examiner* — Annette Dixon
(74) *Attorney, Agent, or Firm* — Lerner, David, Littenberg, Krumholz & Mentlik, LLP (57) ABSTRACT

The invention features methods and apparatus for the treatment of asthma patients. A controlled supply of breathable air delivered to a patient interface or mask (4) is controlled for patient comfort to maintain a steady pressure level in a range 2 to 4 cm H2O to accommodate patient respiration. The breathable air is cleaned by a high efficiency particulate arresting filter (10) to remove allergens from the air supply. The apparatus may be programmed to automatically detect asthma-related symptoms such as an asthma attack by analyzing the respiratory flow of the patient. In response to the detection of such an attack, the apparatus may provide an audible warning or if configured with a treatment delivery module (14A, 14B), the device may administer a therapeutically effective dose of a drug or substance, for example, a broncho-dilator, to alleviate the patient's breathing difficulty. Preferred mask designs allow for proper CO2 washout to accommodate the low pressures supplied to the mask and prevent asphyxia.

30 Claims, 6 Drawing Sheets

(56) References Cited

U.S. PATENT DOCUMENTS

| | | | |
|---|---|---|---|
| 4,971,052 A | | 11/1990 | Edwards |
| 5,186,166 A | | 2/1993 | Riggs et al. |
| 5,413,097 A | | 5/1995 | Birenheide et al. |
| 5,485,827 A | * | 1/1996 | Zapol et al. ............. 128/200.14 |
| 5,540,225 A | * | 7/1996 | Schutt .................... 128/207.15 |
| 5,577,496 A | | 11/1996 | Blackwood et al. |
| 5,645,054 A | | 7/1997 | Cotner et al. |
| 5,704,345 A | | 1/1998 | Berthon-Jones |
| 5,776,213 A | | 7/1998 | Flaherty et al. |
| 5,873,359 A | | 2/1999 | Zapol et al. |
| 5,896,857 A | | 4/1999 | Hely et al. |
| 5,950,621 A | | 9/1999 | Klockseth et al. |
| 6,029,660 A | | 2/2000 | Calluaud et al. |
| 6,041,777 A | * | 3/2000 | Faithfull et al. .......... 128/200.24 |
| 6,189,532 B1 | | 2/2001 | Hely et al. |
| 6,286,508 B1 | | 9/2001 | Remmers et al. |
| 6,289,974 B1 | | 9/2001 | DeGregoria et al. |
| 6,349,724 B1 | | 2/2002 | Burton et al. |
| 6,561,190 B1 | * | 5/2003 | Kwok .................... 128/207.12 |
| 6,581,594 B1 | | 6/2003 | Drew et al. |

FOREIGN PATENT DOCUMENTS

| | | |
|---|---|---|
| DE | 19626924 A1 | 1/1998 |
| EP | 241188 A1 | 10/1987 |
| EP | 334555 A2 | 9/1989 |
| GB | 2300814 A | 11/1996 |
| WO | 9706843 A1 | 2/1997 |
| WO | 98/06449 | 2/1998 |
| WO | 98/12965 | 4/1998 |
| WO | 98/25662 | 6/1998 |
| WO | WO 99/12635 A1 | 3/1999 |
| WO | 9964747 A1 | 12/1999 |
| WO | 0027457 A1 | 5/2000 |
| WO | 00/38772 | 7/2000 |

OTHER PUBLICATIONS

Beers, Mark H. and Robert Berkow Eds. "Section 6—Pulmonary Disorders—Chapter 76:Hypersensitivity Diseases of the Lungs". The Merck Manual of Diagnosis and Therapy. 17th Edition. Merck Research Laboratories, 1999. p. 627-634.*

International Search Report for Application No. PCT/AU02/00161 dated Apr. 26, 2002.

* cited by examiner

METHODS AND APPARATUS FOR SUPPLYING CLEAN BREATHABLE GAS

This application claims the priority filing date of Australian provisional patent application serial number PR3154 filed on Feb. 16, 2001.

FIELD OF THE INVENTION

The invention relates to a method and apparatus for providing a supply of clean breathable gas particularly during sleep. More specifically, the invention relates to devices that may be used to detect, diagnose, treat, manage and/or prevent asthma symptoms in patients.

BACKGROUND OF THE INVENTION

Figure 1:
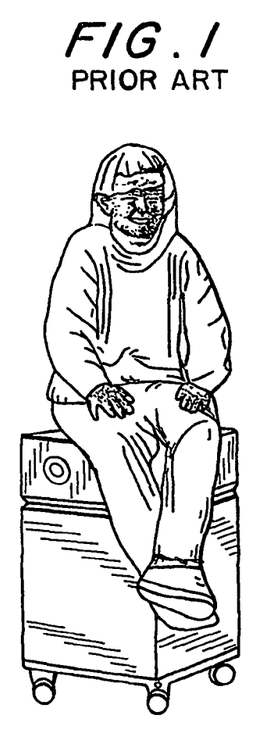
FIG. 1 shows a prior art device for air filtration.

The presence of airborne particles such as pollen, fungal spores and dust mites in bedrooms is associated with respiratory diseases such as asthma. The United States National Institutes of Health (NIH) recommends removing such things as pets, rugs, carpets and curtains to reduce the presence of allergens in the bedroom (NIEHS Fact Sheet #9, ASTHMA, 7/97). A known solution is to place an air filter in the bedroom such as the Austin Healthmate which includes HEPA (High Efficiency Particulate Arresting) filters and activated carbon. HEPA technology is described in U.S. Pat. Nos. 4,629,482, 4,685,944 and 6,289,974. Such air filters are provided as free-standing units as shown in FIG. 1. These devices are said to clean the air in a typical sized bedroom in 15 to 30 minutes. Known problems with such devices include that they can be too noisy to run continuously while a person is attempting to sleep in the same room, as well as the possibility of the room becoming recontaminated every time that the door, windows or ventilation ducts are opened.

A known acute therapy for asthma is oral delivery of a broncho-dilator such as albuterol (also known as salbutamol). One form of this drug is Ventolin™ manufactured by SmithKline Beecham. Another example of a therapy used for the treatment of asthma is the delivery of a vasodilator such as a therapeutically effective amount of nitric oxide as disclosed in U.S. Pat. No. 5,873,359.

SUMMARY OF THE INVENTION

The invention features an apparatus for providing a supply of clean breathable gas that is designed for those who suffer from asthma. The apparatus includes a blower with an allergen filter, such as a HEPA filter, an air delivery conduit and a patient interface, and may be conveniently designed for portable or outpatient use. The blower provides air to the patient interface at a preferred range of pressure from 1 to 4 cm $H_2O$. The blower includes a flow meter for monitoring the flow of air to and from the patient. The apparatus may include a controller such as a microprocessor for analyzing the flow signal to determine asthma-related symptoms, for example, by calculating an index of roundness or flatness of the flow curve, or both, which may be indicative of the bronchial hyperactivity that characterizes asthma or partial obstruction of the airways. The device also monitors the tidal volume of the patient's respiration. The device may include an alarm for alerting the patient or a care-giver that the person using the device may be suffering an asthma attack. In another embodiment, the device includes apparatus for delivering to the patient a dose of a therapeutic drug or other therapeutically-effective substance. In one form, the delivery of oxygen or other therapeutic substance is synchronized with the inspiratory phase of the breathing cycle.

DETAILED DESCRIPTION OF THE INVENTION

Figure 2:
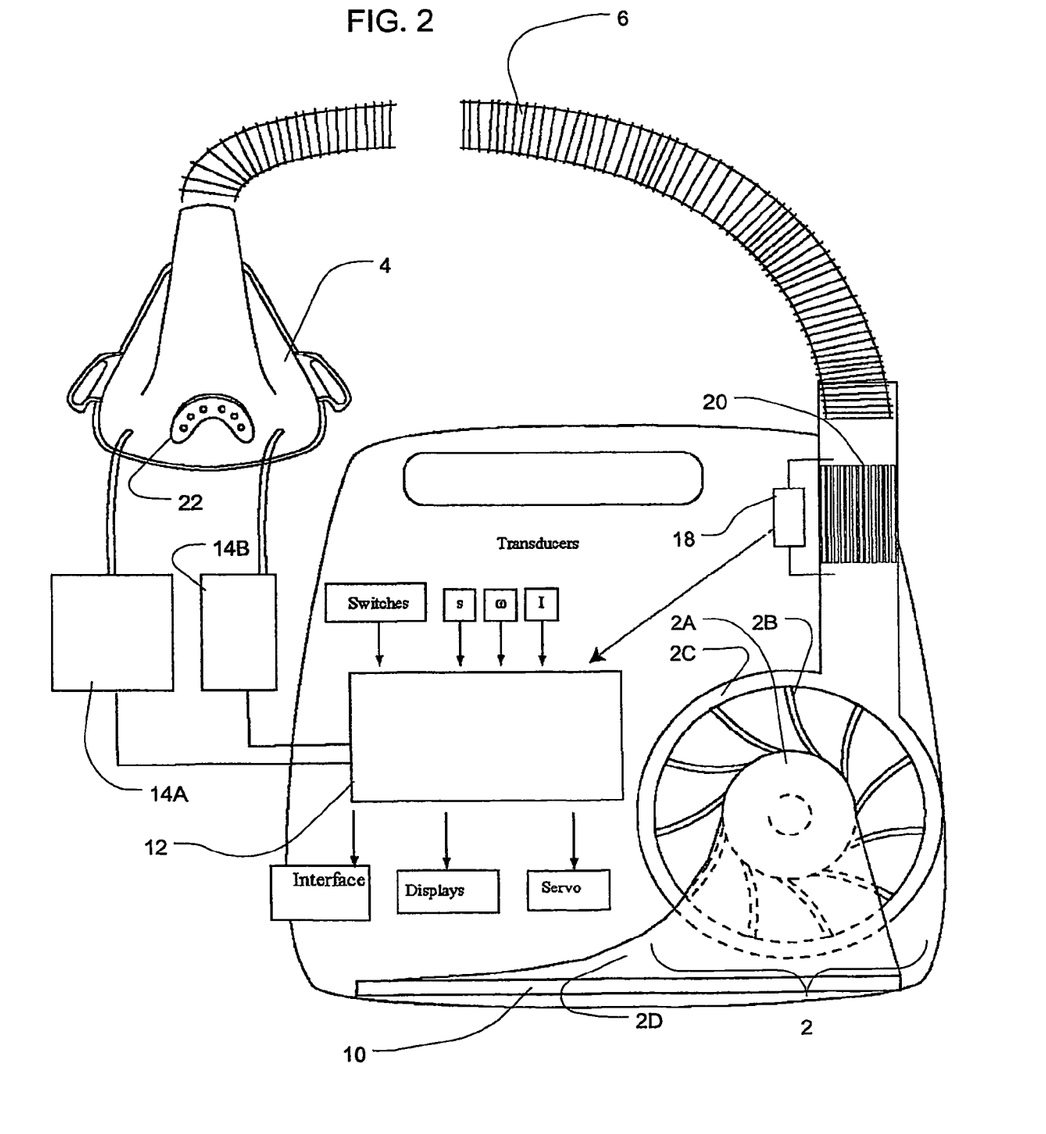
FIG. 2 shows one embodiment of an apparatus according to the invention.

As illustrated in FIG. 2., the asthma treatment/prevention apparatus of the invention includes a blower or other similar device to generate a flow of breathable gas under pressure to a user. The blower 2 supplies breathable gas, such as air, to a patient interface 4, e.g. a mask, via an air delivery conduit 6 as shown in FIG. 2. An example of a suitable blower can be either the RESMED S6™ and S7™ blowers (ResMed Limited). Another suitable blower is found in the AUTOSET T™ and AUTOSET SPIRIT™ devices (ResMed Limited). The blower consists of an electric motor 2A connected to an impeller 2B, the impeller being housed in a suitable volute 2C, for example as described in PCT/AU99/00444.

The blower 2 is designed to have a rising fan curve. This means that as the flow increases, the pressure delivered by the blower increases so as the patient progresses through each cycle of inhalation and exhalation, the mask pressure remains relatively constant. Alternatively, the blower may be process controlled by a controller to implement such a regulation of the mask pressure.

In one form of the invention, the blower motor 2A is a mains voltage AC motor. In this case a power transformer would not be required, reducing the cost of the device. The use of such a motor would dictate a larger impeller than would be the case where the blower uses a lower than mains voltage AC motor or a DC motor. Alternatively, a multistage impeller could be used with the AC motor.

The flow rate must exceed the minimum requirements of breathing to ensure adequate $CO_2$ washout from the patient interface 4. A typical normal patient might have a tidal volume of 0.5 L and a breathing frequency of 10 to 15 breaths per minute. Hence the apparatus must deliver in excess of approximately 10 L/min. In order to allow for coughs or sighs, the flow rate may be several multiples of the minimum breathing requirements. However, the desired $CO_2$ washout flow may dictate a higher flow. In one particularly preferred form the apparatus is designed to have a minimum washout flow of 25 litres/min. The blower 2 of the apparatus in conjunction with the patient interface 4 has the capacity to deliver sufficient flow in an approximate pressure range of 1 cm $H_2O$ to 4 cm $H_2O$ above ambient pressure.

In accordance with the present invention the device may also vary the pressure delivered in the mask from inspiration to expiration (lower for expiration) to assist with the ventilation. A suitable device for this purpose is the VPAP™ positive pressure nasal ventilation device by ResMed Limited. Typically the expiratory pressure (i.e. the mask pressure during expiration) would be set to achieve adequate $CO_2$ washout while the inspiration pressure (i.e. the mask pressure during inspiration) would be set to provide the requisite level of ventilatory assistance. In addition the automatic ventilatory control may be applied to expiration pressure by adopting the techniques taught in U.S. Pat. No. 5,704,345.

Such ventilatory control in the application of the automatic system will monitor and track the patient's ventilation and increase the level of ventilation support when low ventilation is detected based on a continuously updated template of medium term ventilation. Examples of techniques for monitoring ventilation and determining the appropriate ventilatory assist response can be found in PCT/AU97/00631 Berthon-Jones assignee ResMed Limited.

Preferably, the breathable gas that is supplied by the apparatus is substantially free of allergen particles or other asthma symptom-inducing particulates or pollutants. Where ambient air is supplied through the blower 2, the capacity for removing asthma symptom-inducing particulates is provided. Preferably this capacity is provided to function in conjunction with the blower 2 or it may be externally adapted thereto. For example, the blower inlet 2D may include an air cleaning device 10 or filter designed to remove allergens from the ambient air. The air cleaning device 10 or filter may also be designed to remove other air pollutants or particulates. Known air cleaning devices include mechanical filters, electronic filters, hybrid filters (mechanical/electrostatic filters), gas phase filters or ozone generators. A preferred example of a suitable filter for use in the invention is a HEPA filter, alone or in combination with activated carbon. It is generally accepted that a HEPA filter will remove 99.97 percent of airborne particles having a size of 0.3 microns or larger.

The air delivery conduit 6 may be a gas delivery tubing as commonly used with CPAP devices having a cross-sectional diameter of approximately 22 cm. In conventional CPAP treatment it has become generally accepted that a gas delivery tube of at least 22 cm cross-sectional diameter is required to minimize mask pressure swings to a clinically acceptable extent. The pressure swings occur as the patient inhales and exhales. An embodiment of the present invention may operate within a mask pressure range that is typically less than that used in-conventional CPAP for the treatment of, obstructive sleep apnea. For example the pressure range may be between 1.75 cm $H_2O$ and 2.5 cm $H_2O$. In view of this lower mask pressure range used in an embodiment of the present invention it is less susceptible to clinically significant mask pressure swings. In embodiments of the present invention any pressure drop is not of significance so long as the final pressure near the wearer's nose and/or mouth remains slightly above the ambient pressure. In another embodiment of the present invention the tubing used may have a smaller cross-sectional diameter than the tubing used for conventional CPAP therapy and therefore be less bulky. When used in this invention the less bulky tubing will not be unacceptable solely as a consequence of it introducing pressure swings through the breathing cycle. The tubing used must be capable of supplying to the mask gas flow sufficient to meet the patients breathing requirements as well as washing out excess $CO_2$ irrespective of whether it induces pressure swings. The less bulky tubing should facilitate user comfort and ultimately patient compliance.

As previously noted the apparatus is supplied with a patient interface 4. A purpose of the interface 4 is to substantially limit the breathable air of the patient to the gas that is supplied through the apparatus and thereby minimize patient intake of air from alternative sources, such as directly from the ambient environment, which may potentially contain asthma symptom-inducing particulates. The patient interface may be a nasal mask, for example, the MIRAG™ nasal mask (ResMed Ltd). Alternatively the MIRAG™ full-face mask, which covers mouth and nose openings of the patient, may be used as a patient interface. The mask is held in position on the head by headgear constructed from hypoallergenic material. A suitable headgear is the MIRAG™ headgear (ResMed Ltd).

Figure 3:
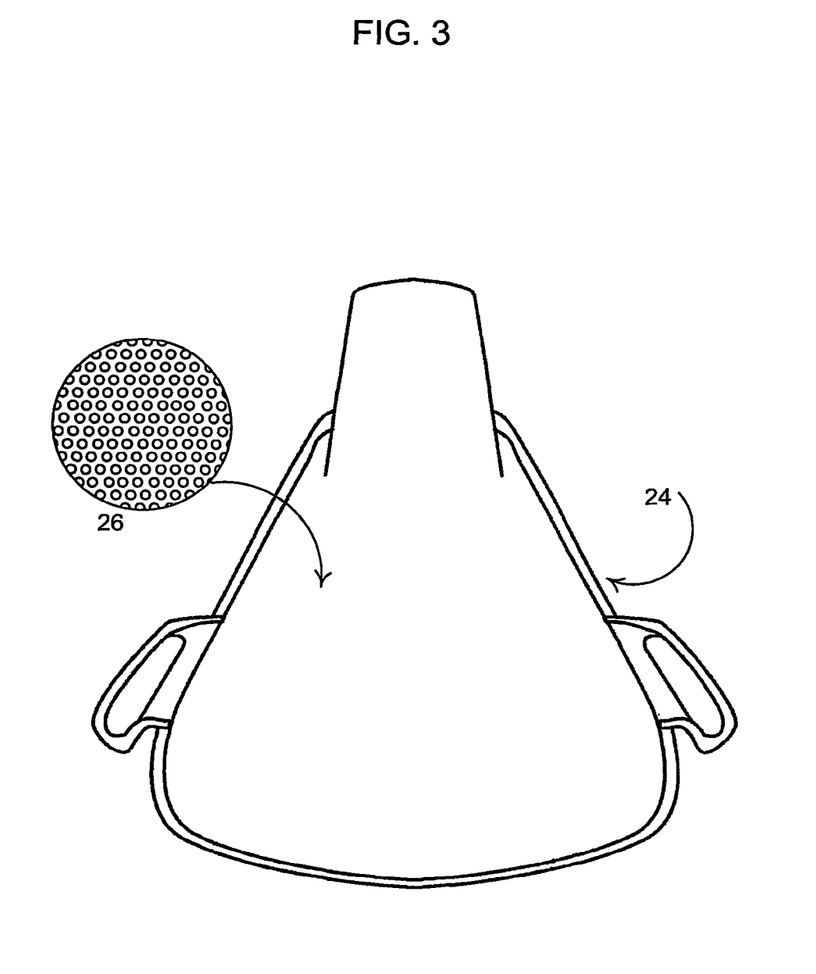
FIG. 3 depicts a porous mask suitable for use with the invention.

In one form, the patient mask is designed to permit a delivery of breathable gas at a pressure of approximately 1 cm $H_2O$ to 4 cm $H_2O$ above ambient pressure. Because of the relatively low pressures in comparison to the application of nasal CPAP for treatment of OSA, the mask may be of a different design to a mask for treating OSA. Referring to FIG. 3, the sealing membrane 24 for a regular CPAP mask is constructed from silicone rubber of 40 durometer hardness, for example, 595 HC manufactured by DOW and may be 0.3 mm to 0.5 mm thick. However, because of the lower treatment pressures used in the present invention, in a mask for the present invention., the thickness may be reduced to 0.1 mm to 0.3 mm. The thinner membrane may lead to greater patient comfort.

In one form, the mask includes a porous rigid frame 26 to allow $CO_2$ washout. In another form, the mask is designed to be totally open when the blower is off, acting as an anti-asphyxia valve. This may be accomplished by constructing the mask with a rigid open frame connected to the air delivery conduit, via, in one form, a swivel or ball and socket joint. The mask also contains a membrane with a generally triangular patient-contacting-portion and a bellows shaped non-patient-contacting portion. When the mask is operating under pressure, the flow of air causes the bellows to expand and seal with the air delivery conduit. When the mask is not operating under pressure, the bellows retract, leaving the patient free to breath ambient air. Other suitable masks with anti-asphyxia valves are disclosed in International Publication no. WO/0038772, U.S. Pat. No. 5,896,857 and 6,189,532. The disclosures of which are hereby incorporated by reference.

In another form of the invention, the mask includes a lockable swivel or ball and socket joint which enables the air delivery tube to be moved about in a number of different positions, but locked into one of these when desired.

Figure 4:
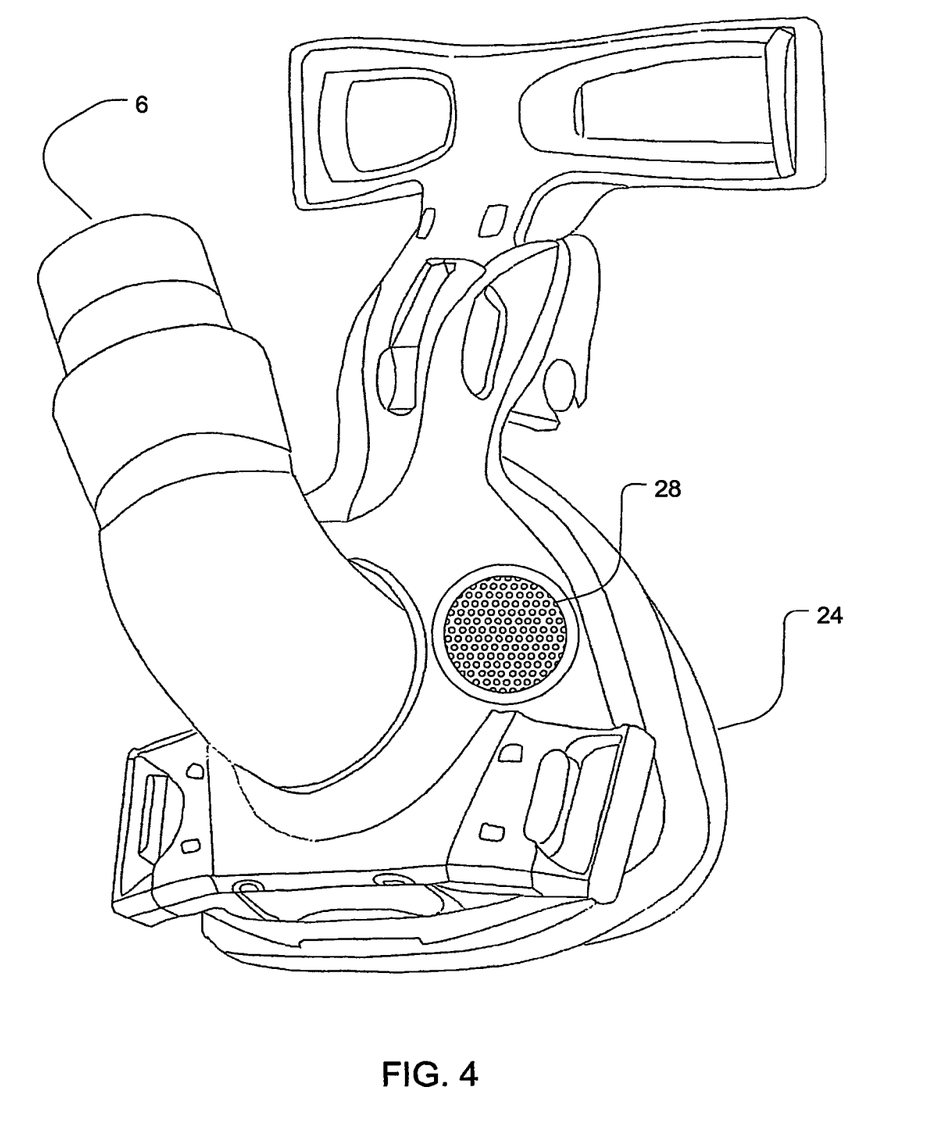
FIG. 4 illustrates another patient interface having a porous portion for use with the invention.

FIG. 4 depicts a polycarbonate mask appropriate for use with the invention. The mask has an addition of two extra vents (only one shown) each consisting of a stainless steel 316 disk 28 secured to the mask shell by way of a silicone grommet which holds the disk in a planer relationship to the mask shell and covers an orifice punched in the mask shell. Each disk is circular, 22 mm diameter, 0.5 mm thick and has 97 circular perforations between its planer sides each perforation being circular 1.2 mm×1.8 pitch. The perforations may be sized to insure adequate $CO_2$ washout and help to prevent asphyxia in the event of blower failure and/or limit the permissible pressure level in the mask. In this way, the mask can provide to the patient a pressure range between 1.75 cm $H_2O$ and 2.5 cm $H_2O$. The mask may also be used in trials and studies in relation to other ventilatory assist techniques. For example to compare the effectiveness of a new therapy in a blind trial fashion against minimal or no therapy. In such applications it is worn by the subject in association with the requisite gas conduit and flow generator. In such a configuration the mask will not deliver to the subject a pressure above its designated top pressure notwithstanding that the flow generator control circuit instructs the flow generator to operate at a level which would deliver a higher pressure had a regular mask been used.

Figure 5:
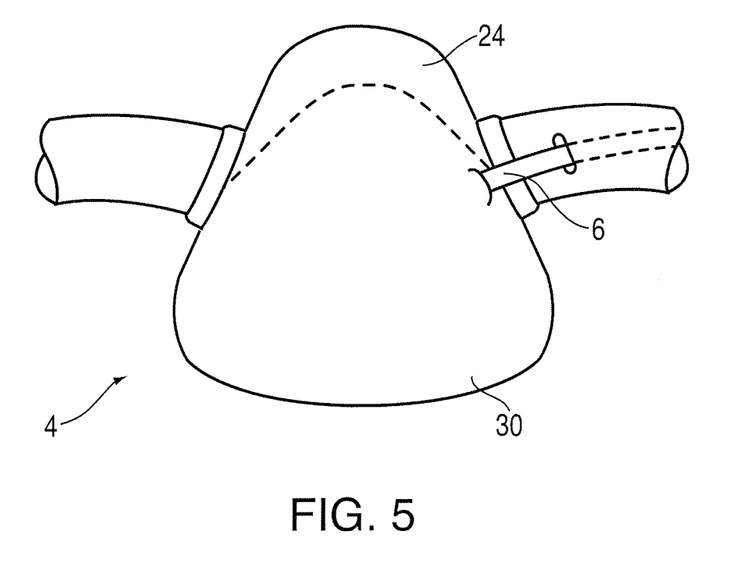
FIG. 5 depicts another patient interface designed in accordance with the goals of the invention.
Figure 6:
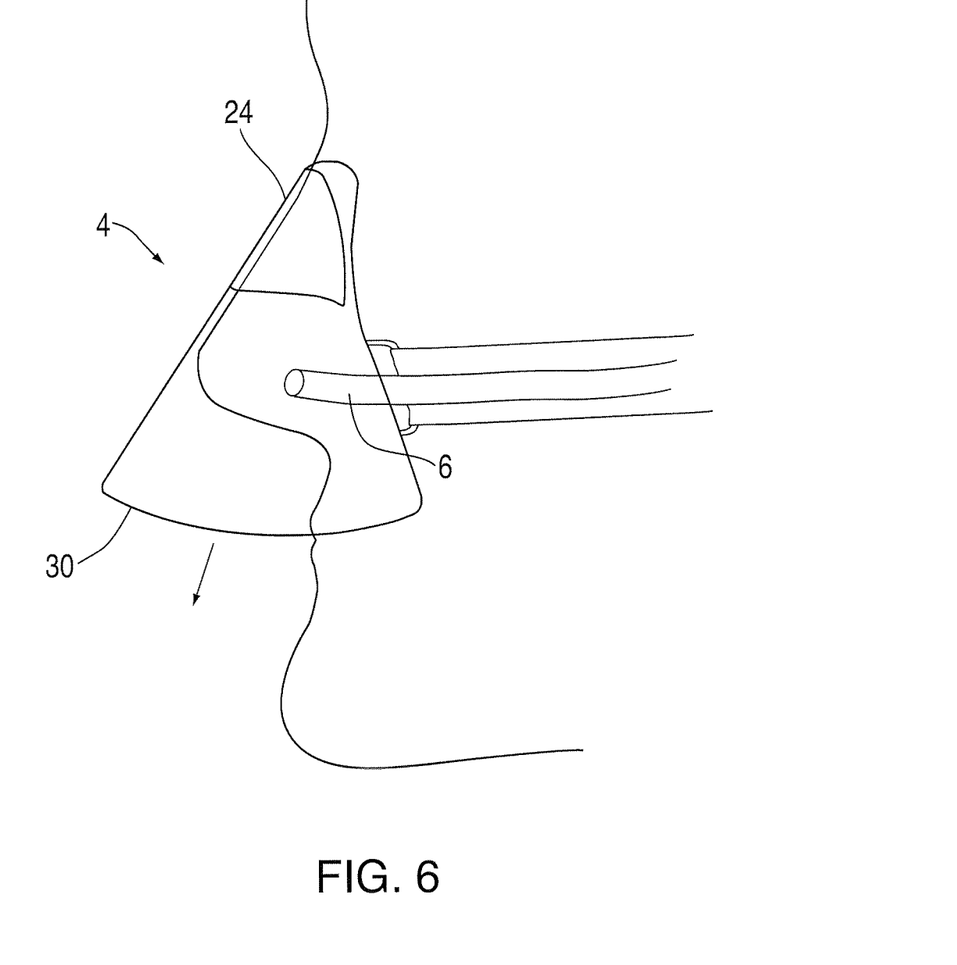
FIG. 6 illustrates the positioning of the mask of FIG. 5 on a user.

In another form of the patient interface, a mask consisting of a shield with a partial cushion designed to seal on the nose may be utilized. Preferably it is positioned on the nose below the nose bridge, so as to avoid that sensitive part of the patient's anatomy. An Illustration of such a mask in accordance with this embodiment can be seen in FIG. 5 and FIG. 6. The sealing membrane 24 is positioned with the intent of preventing gas flow into the user's eyes. The lower part of the mask is open (i.e. is not sealed) and so directs gas downwards over the nares and preferably the mouth so as to provide a 'curtain' of breathable gas. This open lower part 30 of the mask provides washout of exhaled carbon dioxide. It also serves an anti-asphyxia function by providing a safe breathing cavity when the blower is not functioning, thereby negating the need for additional anti-asphyxia components. This interface is designed to be small and light and of minimal impact on the wearer. The intent is to provide a micro atmosphere with a flow of filtered breathable gas that excludes the ambient air to an extent that the patient preferentially breathes the filtered air.

The apparatus of the invention is designed with a controller 12. The controller 12 may include a microprocessor with a medium for programmed instructions or other processor or electronic circuitry to direct the functioning of the apparatus. The controller 12 accepts signals from a flow meter 18, for example, a differential pressure transducer. The controller may also include pressure transducers for sensing pressure levels in the mask. The controller monitors the output from the flow meter, as well as the current to the motor and the number of revolutions per minute of the motor. The controller also controls the display of information on the exterior of the apparatus and is responsive to switches mounted on the exterior.

The controller 12 may be designed to direct the delivery of therapeutic substances, such as a therapeutic gas, drugs and/or supplemental oxygen to the patient interface as further described herein. The device may include a reservoir and pump, or for substances stored under pressure, such as oxygen, a reservoir without a pump. An example of a suitable device for delivery of a therapeutic substance, drug or, oxygen, is described in U.S. Pat. No. 6,029,660 (also disclosed in AU Patent 719758 and PCT AU97/00846). The disclosure of U.S. Pat. No. 6,029,660 is hereby incorporated by reference. Such an apparatus is relatively small compared with the prior art. The therapeutic substance delivery devices 14A, 14B administer treatment to the patient under the control of the controller 12 which may control delivery based upon a predetermined schedule and/or the current condition of the patient. The therapeutic substance, drug or supplemental oxygen may be administered directly in the patient interface 4 or alternatively in the blower 2.

In one embodiment, the flow meter 18 measures flow by a differential pressure transducer. Flow of filtered air from the blower passes through a bundle of small tubes 20 aligned in parallel with the flow from the blower. The pressure difference across the bundle varies according to Bernoulli's law. Hence a measure of the flow of air to the mask (raw flow signal) may be calculated. The patient interface 4 includes a deliberate leak through a vent 22 and also typically there is an unintentional leak around the edges of the seal and through other air delivery conduit joints. Since the volumes of air that the patient inhales and exhales over several breaths is approximately equal, an average flow signal over several breaths will provide a measure of the leakage of air from the system. Alternatively, a low-pass filtered air signal, where the filter constant is longer than several breaths, will provide another estimate of the leakage of air from the system. Alternatively, leak flow may be determined according to PCT/AU97/00517. Having determined the long-term average (or low-pass filtered) leak flow, a measure of the instantaneous respiratory airflow may be obtained by subtracting the long-term average signal from the raw flow signal. The respiratory flow signal is a periodic waveform. By convention, inspiration is a positive flow and expiration is a negative flow. Hence it is possible to estimate the transition points between inspiration and expiration from the zero crossing points. In turn this enables the apparatus to synchronize delivery of therapeutic substances, drugs or supplemental oxygen to the inspiratory phase of the breathing cycle and reduce waste of the substance, drug or oxygen. If administered in the blower, then the delivery must be synchronised to account for any propagation delay through the air delivery conduit.

In one form of the invention, the apparatus may be programmed as an asthma attack or asthma-related symptom detector to trigger treatment or to provide a warning of the occurrence of such an attack or such symptoms. In this embodiment, the microprocessor in the device reads the flow signal and determines on a breath-by-breath basis, an index of the roundness or alternatively flatness of the inspiratory portion of the flow time curve. The inspiratory portion of a normal breath waveform has a round shape. If the inspiratory portion of the waveform is flattened or shaped like a square-wave, then it is indicative of partial obstruction of the airway, for example, constriction or narrowing of the bronchus or other asthma-related narrowing of the airways of the lung. One form of flatness index is the RMS deviation of the inspiratory flow curve from a square wave of the same length and area. One form of roundness index is the RMS deviation from a sine wave of the same length and area. Alternatively, the inspiratory flow curve may be scaled to have unit length and area and compared to square and sine waves of unit dimensions. Examples of the formulae for calculating such indices are disclosed in U.S. Pat. No. 5,704,345 which is hereby incorporated by reference.

An inspiratory waveform which closely resembles a square wave will have a small RMS deviation from that waveform and hence have a small flatness index. Conversely, it will have a larger RMS deviation from the sine wave and have a larger roundness index. An inspiratory waveform which closely resembles a sine wave will have a small RMS deviation from that waveform and hence a small roundness index. Conversely, it will have a larger RMS deviation from a square wave and have a larger flatness index. Hence the device provides an alarm and logs the information when the roundness and flatness indices indicate the presence of partial obstruction when compared with predetermined thresholds. In this way the device can determine physiologic changes in the user's breathing patterns and indicate the onset of changes consistent with the onset or occurrence of an asthma attack.

In another form of the invention, the apparatus monitors the shape of the expiratory portion of the flow time curve. Abnormally shaped expiratory flow time curves are taken to be indications of the presence of a partial obstruction and the device responds by issuing a warning, logging the event and indicating the possible need for therapy. For example, this may be accomplished by analyzing an expiratory waveform to determine a flatness or roundness index.

In an embodiment of the invention, the delivery of therapeutic agents or treatments is monitored and recorded together with time and date stamp and other clinically relevant data including user blood oxygen concentration, environmental conditions such as current allergen load and ambient humidity. This data is then processed and made available, say to the clinician, for review. Reported statistics may include frequency and time distribution of airway events (such as deviation from the desired inspiratory or expiratory flow curve) and therapy doses. This data is used for the management of the patient in accessing their response to therapies and as an aid in determining future therapeutic agent dosing. Should there be identified a set of parameters which correlate with an airway event then the device may be programmed to respond by delivery of a predetermined therapeutic response (say by delivery of a therapeutic agent in a predetermined titration regime or ventilatory assistance) and thereby manage the patients condition in a timely manner. If desired the device can be programmed to act in a proactive manner by recognizing the onset of conditions that have previously resulted in an airway event and deliver the therapeutic response to stabilize the patient prior to the patent having an airway event that warrants a more significant therapeutic response.

The effectiveness of a therapeutics response may be studied by programming the device to only provide a therapeutic response to an identified set of conditions (e.g. patient physiological state or atmospheric conditions or both) on some occasions and not on others. By examination of the monitored data it is possible to determine the effectiveness of the therapeutic response.

In a further embodiment a data management system will build and regularly update templates of patient responses to conditions and therapeutic responses in order to characterize patient responses and thereby provide patient specific data to an expert system decision tree. The decision tree may be used to determine future therapy strategies.

To broaden the system's diagnostic usefulness there may be provided the capacity to eliminate the filtered air reaching the patent so that unfiltered air reaches the patient. This capacity allows for the ability to identify correlations between environmental contaminates and airway events and therapeutic responses.

In another form of the invention, the apparatus is provided with an attachment for spirometry in the mask. The nose is blocked and the patient is instructed to take a deep breath and blow into the tubing in accordance with known techniques for measuring respiratory function. The device measures the flow and pressure and logs the peak flow and the total volume exhaled during the first 1 second of exhalation. The data from these measurements are available for both the patient and physician.

In one embodiment, the apparatus automatically detects the efficiency or status of the air cleaning device. For example, the controller is configured to monitor the impedance of an air filter by monitoring the power required to deliver a certain pressure and flow or some other-measurable function of the blower such as its velocity or r.p.m. As the filter becomes blocked its impedance increases. When the filter impedance has reached a predetermined threshold, a warning is given as an alarm or message display to say that the filter should be replaced. In addition, the apparatus monitors the number of hours of use of the device since some filters ought to be replaced after a fixed number of hours of use. Suitable techniques and algorithms for such monitoring are described in international patent application No. PCT/AU99/0972 (also bearing international publication No. WO00/27457).

In another form of the invention, the apparatus delivers a higher pressure of air to the patient during the inspiratory portion of the patients breathing cycle. In one form, the higher inspiratory pressure is less than 10 cm $H_2O$. When the apparatus is delivering a therapeutic drug, for example by pumping the drug at pressure from a reservoir, the pressure of drug delivery is controlled to be higher than the mask pressure. Hence when the device delivers a higher mask pressure during the inspiratory portion of the patient's breathing cycle, the apparatus automatically increases the pressure of the drug delivery to be higher than the mask pressure by a predetermined offset.

Although the invention has been described with reference to particular embodiments, it is to be understood that these embodiments are merely illustrative of the application of the principles of the invention. Thus it is to be understood that numerous modifications may be made in the illustrative embodiments of the invention and other arrangements may be devised without departing from the spirit and scope of the invention

We claim:

1. An apparatus for the delivery of treatment for a patient with asthma, comprising:
    a blower with an inlet to supply breathable gas to a patient interface,
    a transducer to generate a flow signal representative of flow of the patient,
    a transducer to generate a pressure signal representative of pressure supported by the blower,
    a processor to receive data from said flow signal and said pressure signal with programmed instructions for controlling said blower and to detect an asthma symptom from an analysis of said data, and
    a filter to substantially remove allergen particulates from the breathable gas flow.

2. The apparatus of claim 1 wherein said filter is a high efficiency particulate arresting filter.

3. The apparatus of claim 2 wherein said filter includes activated carbon.

4. The apparatus of claim 3 wherein said patient interface is a porous mask to insure $CO_2$ washout at low pressures that covers the patients nose openings and has a sealing membrane thickness in the range of 0.1 mm to 0.3 mm.

5. The apparatus of claim 4 wherein said processor is further programmed with instructions to assess filter status and to generate a warning when said assessment indicates that the filter should be changed.

6. The apparatus of claim 2 wherein said processor controls said blower so as to vary said flow of breathable gas in response to the patient's respiration to maintain a relatively constant pressure at the patient interface.

7. The apparatus of claim 1 further comprising a controlled means for delivering a therapeutic substance to supplement said flow of breathable gas to the patient.

8. The apparatus of claim 7 wherein said processor is further programmed with instructions for controlling a delivery of the therapeutic substance by said controlled means in response to a detection of a symptom of asthma.

9. The apparatus of claim 8 wherein said therapeutic substance is a bronchodilator.

10. The apparatus of claim 8 wherein said therapeutic substance is a gas.

11. The apparatus of claim 10 wherein said gas is oxygen.

12. A method for treating a patient with asthma, comprising the steps of:
    delivering a controlled supply of breathable air to a patient,
    providing a patient interface that substantially limits the patient's breathable air to the controlled supply of breathable air when it is being supplied through the interface,
    cleaning said breathable air in conjunction with the delivery of said breathable air to the patient to substantially remove allergen particulates from said air before said patient inhales said allergen particulates,
    monitoring air flow of the patient, and
    analyzing said air flow to detect a symptom of asthma.

13. The method of claim 12 wherein said patient interface is a porous mask to insure $CO_2$ washout at low pressures that is adapted to cover the patient's nose openings.

14. The method of claim 12 wherein said patient interface permits a breathable flow of ambient air when said controlled supply of breathable air ceases.

15. The method of claim 13 wherein said controlled supply of breathable air varies in response to the patient's respiration to maintain a relatively constant pressure at the patient interface.

16. The method of claim 15 wherein said controlled supply of breathable air is varied in a range of pressure from 1.75 to 2.5 cm $H_2O$ at the mask.

17. The method of claim 16 wherein said filter is a high efficiency particulate arresting filter.

18. The method of claim 17 wherein said filter includes activated carbon.

19. The method of claim 18 wherein said therapeutic substance is a broncho-dilator.

20. The method of claim 17 further comprising the step of assessing the condition of the filter to determine whether the filter should be changed.

21. The method of claim 20 wherein said step of assessing involves calculating the impedance of the filter.

22. The method of claim 21 wherein said impedance is a function of the blower's power consumption.

23. The method of claim 17 wherein said step of analyzing said air flow to detect a symptom of asthma includes the sub-steps of:
    calculating a shape index from data representing a portion of said air flow; and
    comparing said index to a predetermined threshold.

24. The method of claim 23 wherein said shape index is an indicator of the flatness of an inspiratory portion of patient flow.

25. The method of claim 23 wherein said shape index is an indicator of the roundness of an inspiratory portion of patient flow.

26. The method of claim 23 wherein said shape index is an indicator of the flatness of an expiratory portion of patient flow.

27. The method of claim 23 wherein said shape index is an indicator of the roundness of an expiratory portion of patient flow.

28. The method of claim 15 further comprising the step of administering a therapeutic substance to the patient through the patient interface in response to said detection of a symptom of asthma.

29. The method of claim 28 wherein said therapeutic substance is a gas.

30. The method of claim 29 wherein said gas is oxygen.

* * * * *